United States Patent [19]

Thorson et al.

[11] Patent Number: 4,680,450
[45] Date of Patent: Jul. 14, 1987

[54] APPARATUS FOR CONTROLLING THE HEATING OF COMPOSITE MATERIALS

[75] Inventors: Russell E. Thorson, Outagamie County; Douglas J. Marver, Marathon County, both of Wis.

[73] Assignee: Kimberly-Clark Corporation, Neenah, Wis.

[21] Appl. No.: 760,441

[22] Filed: Jul. 30, 1985

[51] Int. Cl.$^4$ .......................................... F27D 11/00
[52] U.S. Cl. ................................... 219/388; 219/411; 219/354; 219/343
[58] Field of Search ................ 219/388, 388 S, 354, 219/405, 411, 400, 402, 403, 343; 198/803.13, 484.1; 264/230, DIG. 71; 425/174.4; 156/85, 161, 164

[56] References Cited

U.S. PATENT DOCUMENTS

| | | | |
|---|---|---|---|
| 784,854 | 3/1805 | Grace | 219/388 |
| 2,186,566 | 1/1940 | Albright | 219/388 |
| 3,245,407 | 4/1966 | Mason | 128/284 |
| 3,249,741 | 5/1966 | Mills | 219/411 |
| 3,395,786 | 8/1968 | Rosema | 198/484.1 |
| 3,639,917 | 2/1972 | Althouse | 2/270 |
| 3,818,181 | 6/1974 | Benard | 219/388 |
| 3,912,565 | 10/1975 | Koch et al. | 156/85 |
| 4,050,462 | 9/1977 | Woon et al. | 128/287 |
| 4,298,331 | 11/1981 | Mueller | 264/230 |
| 4,300,967 | 11/1981 | Sigl | 156/164 |
| 4,333,003 | 6/1982 | Rivera | 219/354 |

FOREIGN PATENT DOCUMENTS 2016262  9/1979  United Kingdom .
2136678  9/1984  United Kingdom .

OTHER PUBLICATIONS

Perrotta, Frank, "Heating With Far Infra-Red", Plastics Engineering, Aug. 1953, pp. 109-111, 114, 115.
Trad Publication "Process Heat", from GTE-Sylvania, Lighting Products Group-pp. 36-39 & Cover.

Primary Examiner—E. A. Goldberg
Assistant Examiner—Teresa J. Walberg
Attorney, Agent, or Firm—P. A. Leipold; D. L. Traut; J. J. Duggan

[57] ABSTRACT

A heating apparatus at the end of a diaper production line composed of a series of radiant energy sources. These radiant energy sources are controlled so as to emit differing concentrations of radiant energy. The sources are controlled so as to emit radiant energy more absorbent by diaper polymer backing sheets in the first section of the heater and more absorbent by heat-shrinkable diaper elastics in the downstream portion of the heater. Further, the temperature of the heaters is preferably controlled to the desired infrared range by blowing hot air past the heaters and onto the diapers so as to provide conductive transfer and at the same time control the infrared radiant energy that is provided by the heaters.

7 Claims, 7 Drawing Figures

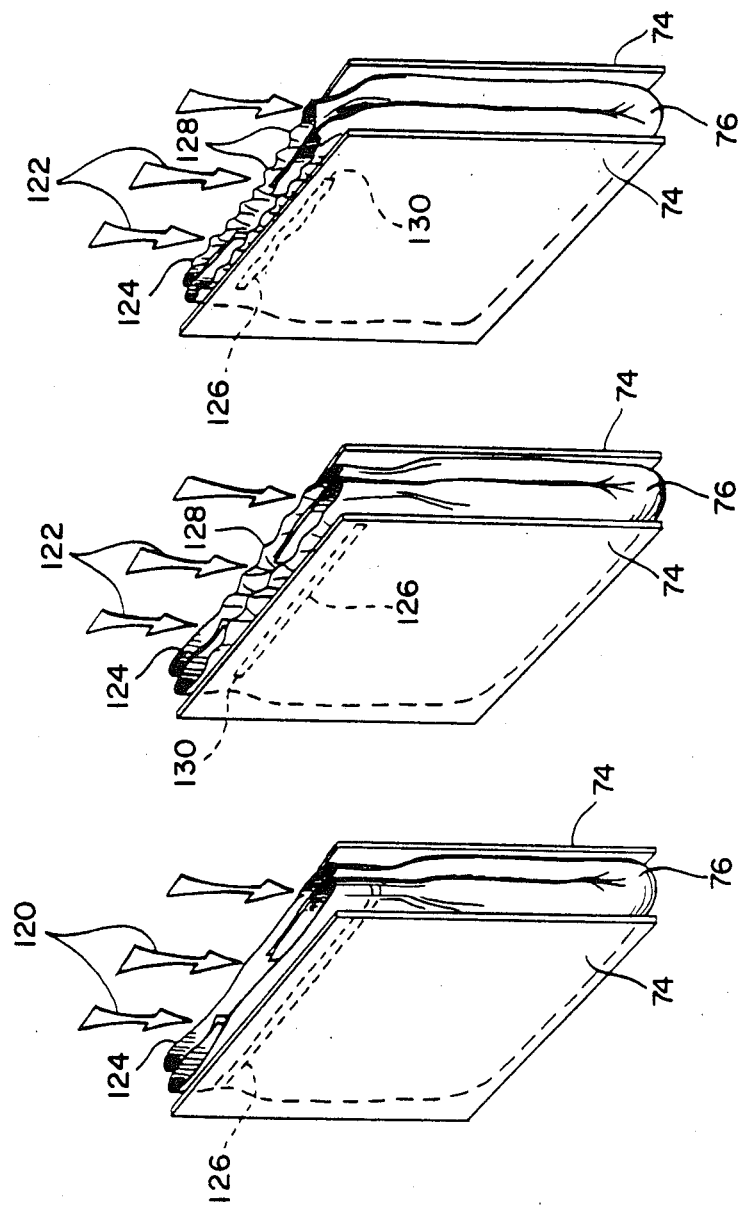

APPARATUS FOR CONTROLLING THE HEATING OF COMPOSITE MATERIALS

TECHNICAL FIELD

The invention generally relates to methods and apparatus for the heating of composite materials by radiant energy. It particularly relates to the combination of zones of infrared energy and hot-air heating of composite materials.

BACKGROUND ART

It has been proposed that heat-shrinkable elastics be used in the formation of disposable garments. such heat-shrinkable elastics are known to find particular use in the formation of waist bands for disposable diapers for incontinent garments. The formation of diaper garments with heat-shrinkable elastic at the waist is illustrated in the method and apparatus of UK patent application No. GB 1,136,678—Chapman et al. In the method and apparatus illustrated there the elastic is placed cross-direction to the movement of the web that forms the backing of the diaper. Subsequent treatment of the discrete articles with heated air at about 68 degrees C. is disclosed as suitable to cause the elastically-contractible elements to shrink.

It is also disclosed in copending U.S. patent application U.S. Ser. No. 605,968, filed May 1, 1984, W. S. Pomplun et al., "Formation of Elasticized Portions of Disposable Garments and Other Articles." The copending application, coassigned with the instant application, discloses a method and apparatus for heating a heat-shrinkable elastomer. The heating method and apparatus utilizes heated air at about 175 degrees F.

It has been proposed in copending application entitled "Method and Apparatus for Activating Heat-shrinkable Ribbon on Disposable Garments and Other Articles," Roland et al., Ser. No. 718,410 filed Apr. 1, 1985, that the method and apparatus for activating the heat-shrinkable material be a source of radiant energy with air flow conditionally contributing to heating of the materials.

While the above methods are believed to be successful, there remain problems with the processes and apparatus. The process of diaper formation is performed at very high speed. During high speed processing all diapers may not be folded in exactly the same manner so that the heat-shrinkable waist materials may be somewhat hidden and not susceptible to good heat transfer by air or direct exposure to the radiant energy. Further, there is a difficulty in that the polymer backing material for a diaper is formed of a low-melting polymer such as polypropylene that will melt if it it heated significantly. The difficulty with prior systems is that at high speeds the elastic may not be adequately exposed to either radiant energy or heated air to cause complete shrinking of the heat shrinkable elastic. Therefore, there remains a need for an improved high-speed system for shrinkage, particularly for the elastic at diaper waist.

DISCLOSURE OF THE INVENTION

It is an object of this invention to overcome the disadvantages of prior processes and apparatus.

It is another object of this invention to selectively heat composite articles.

It is a further object of this invention to produce uniformly shrunk elastic waist diapers.

It is an additional object of this invention to provide for high-speed shrinking of heat-shrinkable elastics on polymer backings.

An additional further object of this invention is to provide improved elastic waist diapers.

The invention is generally accomplished by providing heating apparatus at the end of a diaper production line that comprises a series of radiant energy sources. These radiant energy sources are controlled so as to emit differing concentrations of radiant energy. The sources are controlled so as to emit radiant energy more absorbent by the polymer backing sheets in the upstream first section of the heater and more absorbent by the heat-shrinkable elastics in the downstream second portion of the heater. Further, the temperature of the heaters is preferably controlled to the desired infrared emitting ranges by blowing air past the heaters and onto the diapers so as to provide conductive heat transfer to the diapers and at the same time cool the heaters and control the wave length of infrared radiant energy that is provided by the heaters.

BRIEF DESCRIPTION OF THE DRAWINGS

FIGS. 5, 6, and 7 are views of the diaper as it is shrunk.

MODES FOR CARRYING OUT THE INVENTION

The system of the invention has numerous advantages over prior systems. The system of the invention utilizes ceramic heater elements that are of long life and if broken do not shatter to create harmful materials in the diapers. The devices of the invention utilize the heated air both as heating medium for the diaper and heat-shrinkable elastic, and as a cooling medium for the heaters in order to control the temperature of the heaters and thereby control the wave length of radiant energy emitted by the heaters. The system of the invention further is suitable for operation at high speed up to at least 400 diapers per minute. Another advantage is that by control of the heating process to first heat the polymer backing material the shrinking of the elastic is more effective as the polymer, softened by the heating, easily contracts. Another advantage of the instant system is that it allows close control of the temperature in the heater so that excessive heating is not possible. Further, the apparatus of the invention provides that the heaters are focused and that the infrared radiant energy applied to the diapers may be quickly decreased by withdrawal of the heaters. These and other advantages will become apparent from the detailed description below and the drawings attached.

Figure 1:
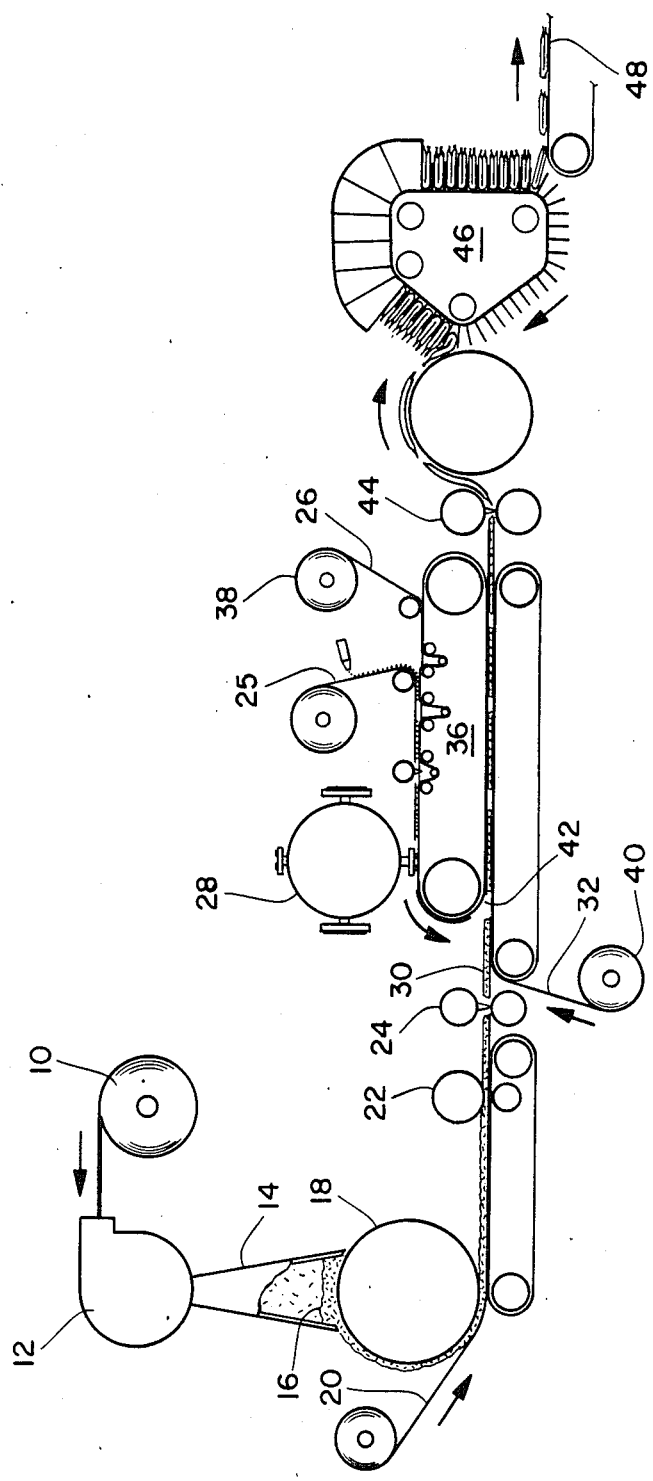
FIG. 1 is a schematic illustration of a diaper formation process and apparatus.

Illustrated in FIG. 1 is a schematic view of the diaper assembly process and apparatus. Device 10 represents the source of pulp sheet which is fed to the fiberizer 12 where the pulp is divellicated and falls through chute 14 to collect in a pile 16 at the top of forming drum 18. The drum 18 is provided with a source of vacuum, not shown, that draws the divellicated fibers of pulp onto a foraminous member or connected series of members on the outside of the drum 18. The pulp fluff formed on the drum is removed from the drum and placed onto the scrim sheet 20, where it is carried through debulking rolls 22 and cutters 24, where it is cut into individual pieces for placement on a diaper. If the pad is not formed in the shape suitable for diaper use having leg cutouts, a cutting device to shape the pad may also be provided. The waist elastics 25 may be applied to the polymer backing material 26 by the applicator device 28. The separated absorbent members 30 are placed on a permeable member 32 that forms the inner permeable side of the diaper. The impermeable backing member 26 has leg elastic applied by device 36. The impermeable backing is withdrawn from source 38, while the permeable body-side liner is withdrawn from source 40. The permeable member 32, fluff absorbent member 30, and impermeable backing 26 are united at 42. At 44 the web of diapers is cut into individual diapers and placed into the heater and conveyor device 46. Not shown is the conventional apparatus for applying tapes to the diapers for fastening and the device for making leg cutouts. These devices are known and are not a part of the instant invention. Other parts of the assembly not shown but conventional are the construction adhesives utilized to adhere the shrinkable elastic and leg elastics to the diaper as well as to hold the fluff pad in place. After heating in device 46, the diapers are placed onto a conveyor 48 and taken for bagging prior to warehousing and distribution. The invention relates to the elastic waist of the diaper and the shape of the absorbent or placement of leg elastic are matters of choice.

Figure 2:
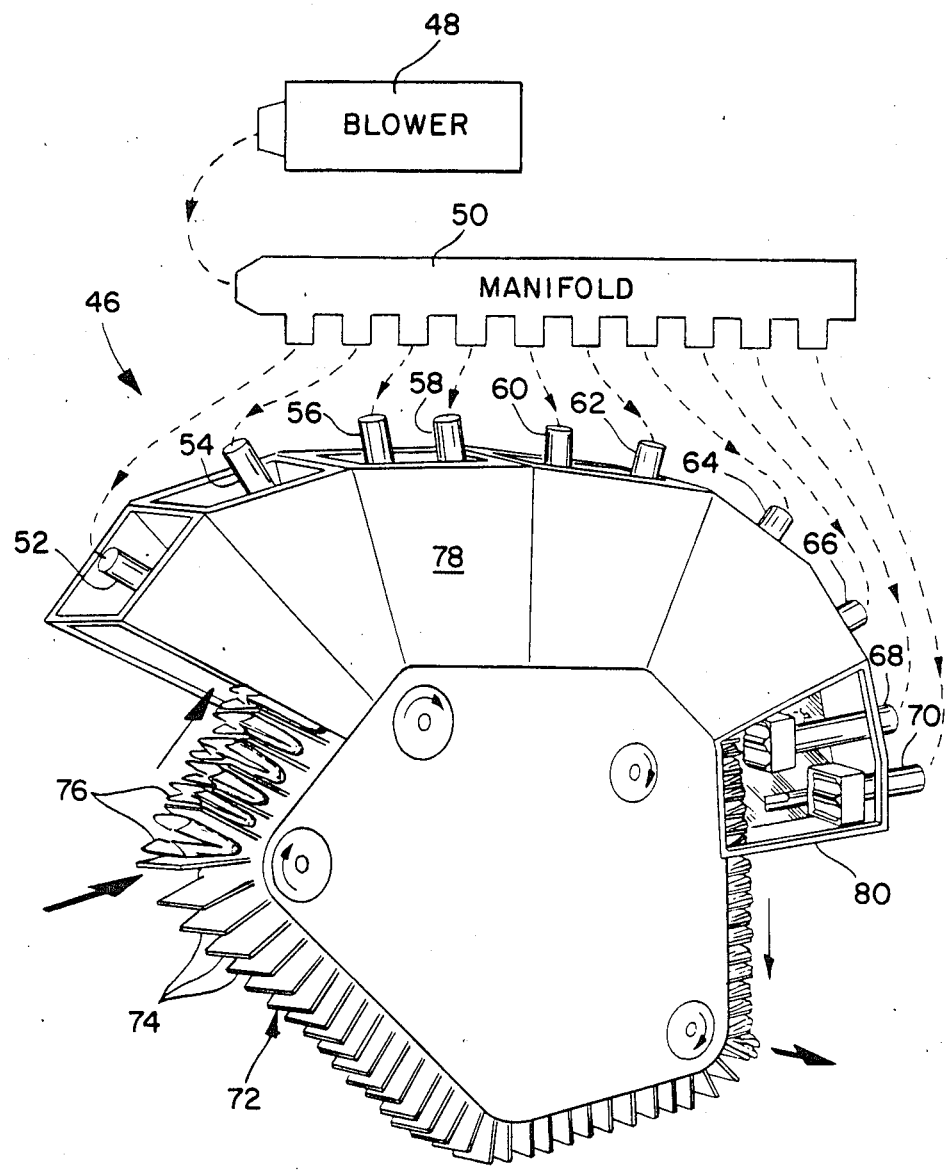
FIG. 2 is a partially schematic view of the heater of the invention.

In FIG. 2 is illustrated the conveyor and heater 46. The heat device is provided with a suitable air heater and blower 48, leading to manifold 50 that provides heated air to individual units 52, 54, 56, 58, 60, 62, 64, 66, 68, and 70. The heating and conveying device 46 is provided with a conveyor 72 that has individual flaps 74. Diapers 76 are placed between individual flaps 74 of the conveyor and moved through the enclosed shrinking device 78.

Figure 3:
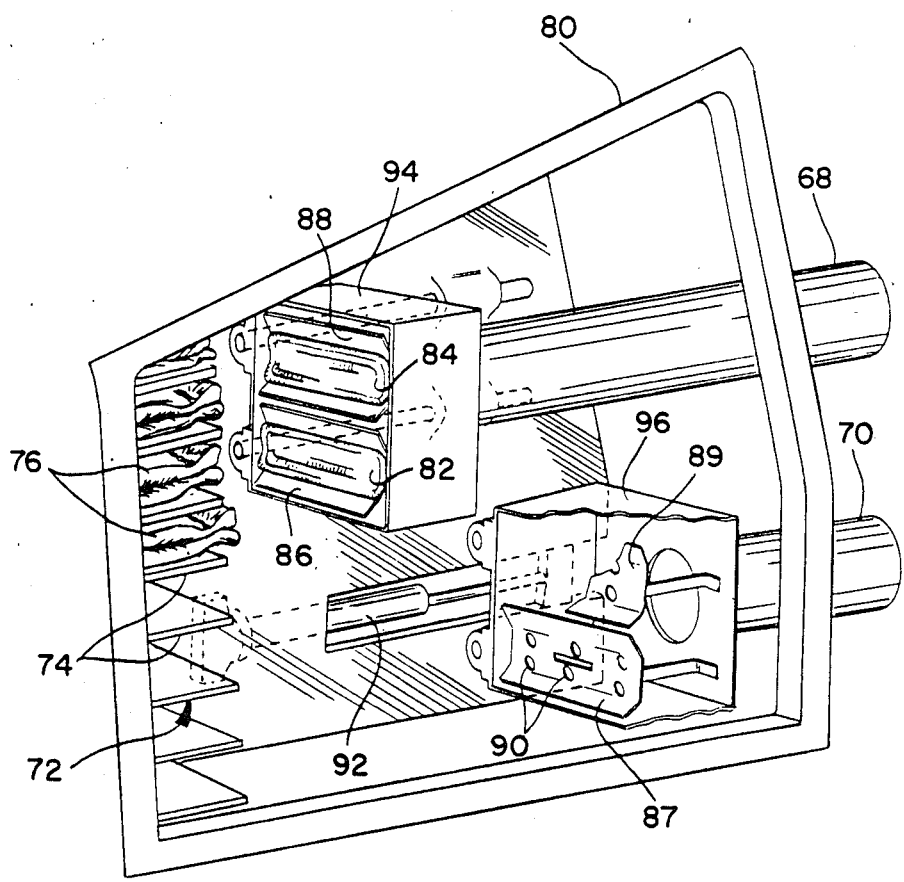
FIG. 3 illustrates the heater units of the invention.

As illustrated in FIG. 3, section 80 of heater conveyor 46 is composed of two movable heater units 68 and 70, each having attached thereto two heaters. Heaters 82 and 84 are attached to heater unit 68. Each of the heaters is backed by a metal plate 86 and 88 respectively. These plates as shown by plates 87 and 89, have holes 90. Heated air enters through heated air inlets of units 68 and 70 and passes over around and through the backing plates such as 86, 87, 88 and 89. Air passing through the foraminous backing plate serves to cool the radiant heaters 82 and 84. Air flow is controlled by means not shown, to provide the correct amount of flow to regulate the temperature of the heater to achieve the preferred spectrum to heat the substrate passing beneath the heater. Airflow may be regulated by conventional means such as controlling fan speed or vanes in the ducts. It is noted that heaters 82 and 84 are curved so as to focus the infrared radiation at the most effective distance from the waist of the diapers carried between vanes 74 of the conveyor 72. The heaters 82 and 84 are arranged in container 94. The containers 94 and 96 are capable of being moved closer or more distant from the diapers carried between vanes 74 by piston 92. Piston 92 may be hydraulic or pneumatically controlled. The unit 94 is shown in position where the infrared radiation is focused upon the waist area of the diapers 76 traveling on the conveyor 72 whereas unit 96 is shown as having been withdrawn. The units 94 and 96 would be withdrawn when the conveyor was stopped to prevent overheating. Further, the units would be withdrawn if the conveyor was operating very slowly or if a material not requiring a great deal of heat was being transported. Further, partial withdrawal could be used to focus the infrared radiation.

Figure 4:
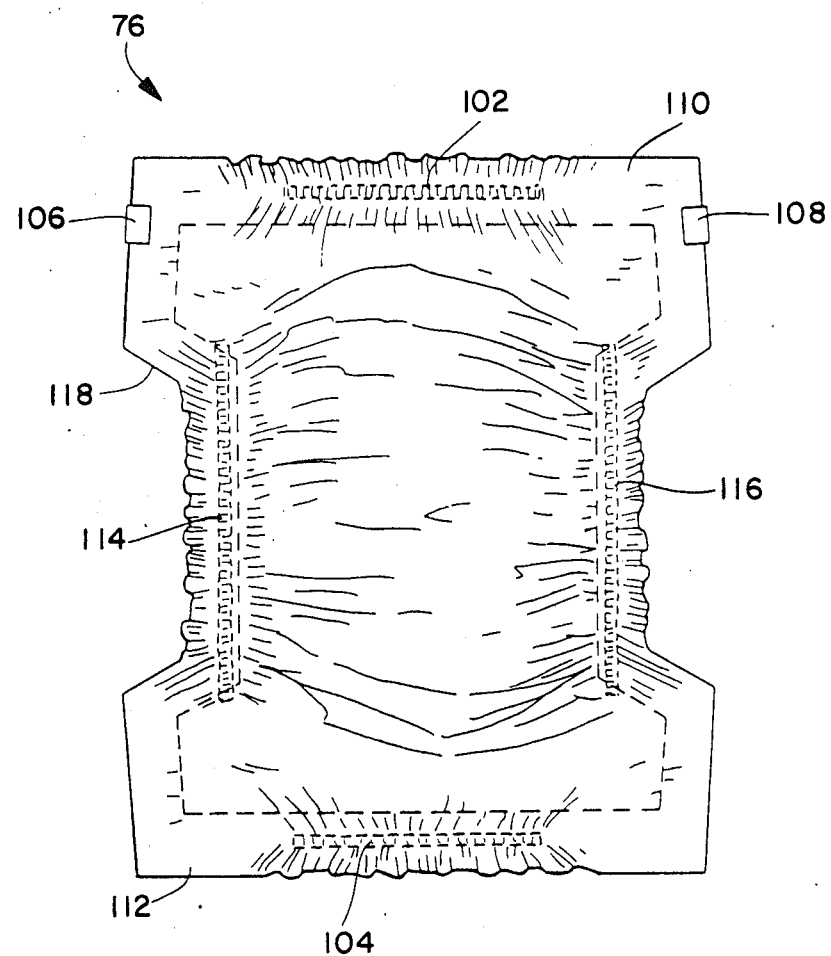
FIG. 4 is a plan view of a diaper with elastic waist and legs.

FIG. 4 illustrates a plane view of a diaper that may be formed by the apparatus and method of the invention. The diaper has elastic at the back waist 102 and front waist 104. The diaper further has tapes 106 and 108, located on back section 110. The tapes when the diaper is in use are fastened onto the front section 112. The diaper has leg elastics 114 and 116 in the crotch portion. There is a leg cutout 118. The diaper is formed in the conventional manner with an impervious backing member forming the outer surface, an absorbent material such as wood fluff forming the center portion, and a water-permeable body-side liner forming the inner surface.

Illustrated in FIGS. 5, 6 and 7 is diaper 56 that is subjected to infrared radiant heat represented by arrows 120. As illustrated in FIG. 5, infrared radiant heat 120 is adjusted so as to be more readily absorbed by the polymer 124, forming the backing sheet of the diaper. This radiant heat serves to soften the polymer sheet at the diaper end exposed between flaps 74. In FIGS. 6 and 7 the infrared radiant heat 122 is adjusted to be of a greater component of a wave length that is particularly absorbable by the heatshrinkable elastic 126, and as the elastic starts to shrink, wrinkles 128 appear in the waist portion of the diaper. FIG. 7 is in the final stages of shrinkage, in which the elastic 126 has shrunk so that end 130 has moved inward, causing a series of wrinkles 128 in the polymer 124 at the waist band.

The infrared heaters utilized in the invention may be any heater that gives off infrared radiation in the desired wave length for the particular material being heated. Typical heaters are disclosed in earlier copending and coassigned application Ser. No. 718,410 filed Apr. 1, 1985, which is hereby incorporated by reference. It is generally preferred that the heaters be of a ceramic material as they are of long life and will not shatter, releasing sharp harmful materials as glass or glass-protected heaters will. Particularly preferred for the instant invention are the Far-Infrared ceramic heaters available from GTE TM Sylvania TM as Model 1FR03107. These heaters are composed of electrical ceramic that has embedded therein a nickel-chrome alloy heater element. The embedded heater element helps the element hang together, even if the ceramic becomes cracked. It is preferred for softening of diaper polymer backing materials that the ceramic heaters be regulated to about 550° C. by air passing over them as to emit predominantly 3.5 micron wave length infrared in the first section of the heater to soften the polypropylene polymer of the diaper. The material when softened aids in effective shrinking and increases the ease of complete shrinking of the heat-shrinkable elastic.

By predominant wave length of about 3.5 micron it is meant that the heater puts out a wave length that has energy given off that is 60 percent of a wave length between about 3.0 microns and about about 4.0 microns.

The ceramic heaters are preferably regulated in the downstream shrinking section to provide radiant energy in a wave length of predominantly about 5.5 microns to shrink the tapes. In order to do this, the heater is regulated by air passing over it to be at a temperature of about 250° C. By predominantly about 5.5 microns it is meant that 60 percent of the radiant energy emitted is between about 4.9 and about 6.1 microns in length.

The heaters are formed so that the focal length is about 3 inches. The heaters are withdrawn to a distance of about one foot when not in use to minimize the application of heat to stationary diapers.

The air flow over the heaters varies with the amount of power being put to the heater. However, it is generally desirable for maximum efficiency that each heater be used at its full-rated power and that cooling air be applied to regulate the temperature to the desired range to emit the preferred wave length of infrared energy. The lowering of the temperature by air cooling while full power is applied to the heater results in the narrowing of the band of emitted infrared rays whereas merely lowering the power to the infrared heater results in a broad band that has shifted in wave length from that of the band emitted higher temperature and higher power.

The heat-shrinkable elastic utilized in the process of the invention may be any desired heat-shrinkable elastic. Exemplary of such materials are those shown in U.S. Pat. No. 3,912,565 to Koch et al. issued Oct. 14, 1975, U.S. Pat. No. 3,639,917 to Althouse issued on Feb. 8, 1972, and U.S. Pat. No. 3,819,401 issued to Massengale on June 25, 1974. A particularly preferred material as it results in the desired amount of elasticity for use in the waist of a diaper as well as being heat shrinkable by rapid heating in response to infrared energy is the elastic material of U.S. patent application, Ser. No. 606,082, date filed May 1, 1984, inventors Matray and Pomplun, that is coassigned and copending with the instant application. This material is a combination of a heat-shrinkable elastomer that has been coextruded with polymer surface layers that are acceptable to adhesively connect the material to a backing. The cover layers prevent the sticky elastomeric material from sticking when wound in rolls and has good adherence to adhesives. This material is particularly desirable as it will shrink when heated but may be stretched at ambient temperatures where it will set in the extended condition but return to a shorter elastomeric length when heated. The disclosure of U.S. Ser. No. 606,082 filed May 1, 1984, is hereby incorporated by reference.

The preferred diaper as set forth above has in addition to the elastic waist shrunk by the process and apparatus of the invention also elastic legs for sealing against leakage at the crotch. Such diapers are well-known in the art and have been disclosed in patents such as U.S. Pat. No. 4,324,245, Mesek et al., and U.S. Pat. No. 4,352,355 to Mesek et al. The method of attaching elastic to the crotch portions of the diapers is disclosed in U.S. Pat. No. 3,860,003 Buell as well as U.S. Pat. No. 4,227,952—Sabee. The methods of placement of the leg or crotch elastics are well known and do not form a part of this invention.

While the invention has been specifically described with respect to the heat shrinking of diaper waist materials, it is suitable for any process in which the control of infrared heating of a composite is desirable. In forming of the elastic-waist diaper, it is desirable that the backing polymer be softened prior to heating of the heat-shrinkable material in order that the shrinking of the elastic material will be more effective on the softened substrate. There are other instances where it may be desirable that a composite article be heated by separate infrared sources. For instance, if one portion of the composite to be heated is very large, it may be desirable that this portion be heated sooner in order to prevent overheating of the smaller portion. In this case, the beginning of the heater would have the infrared heaters tuned to the wave length radiation that the larger piece is susceptible to, while the latter portion of the heater would be tuned to emit the infrared radiation that the smaller portion is susceptible to. In other instances there may be a wide disparity between the susceptibility of the composite material to infrared radiation. Therefore, use of a single broad band radiant heater would be wasteful of energy whereas if two tuned radiant heaters are utilized, less energy is necessary in order to carry out heating.

Further, while the particular heat-shrinkable elastic preferred in this invention has susceptibility to a certain wave length, it is within the invention to regulate the heaters to wave lengths of other elastics such as those of the above-referred to Althouse patent or the blend of ethylene propylene rubber with ethyl vinylacetate as set forth in the above-referred to UK Patent Application GB No. 2,136,678 are susceptible to for heating.

The method and apparatus of the invention may be operated at any desirable combination of air flow and infrared energy application. However, it has been found that the speed of about 600 diapers per minute that an air flow of about 120 cubic feet of air heated at about 220° F. temperature is suitable. The heaters furthermore are operated with 8 GTE IFR0107 heaters in four panels cooled to 550° C. temperature at which they emit the preferred predominant wave length of 3.5 microns and 10 heaters in five panels cooled to a temperature at which they emit the predominantly 5.5 micron's wave length after the heatshrinkable material shrinks. Each heater uses about 500 watts of electrical energy and each panel of two heaters about 1000 watts of electrical energy. The heated air is provided by a blower passing air over heated ceramic rods. The preferred ceramic heaters focus at a distance of about 3 inches from the waist ends of the diapers.

While not illustrated, it is considered desirable that heated air be withdrawn from the interior of the conveyor and recycled for further heating for purposes of conservation.

It will be understood that the foregoing description of the present invention is for purposes of illustration only, and that the invention is susceptible to a number of modifications or changes. For instance, as set forth above, the heated air could be recycled. Further, while the device is shown with a specific number of heaters, the number of heaters and length of the heating section could be adjusted depending on the speed of diaper formation as well as the conveyor length available for heating. The invention is intended to be limited by the scope of the claims attached hereto.

We claim:

1. Apparatus for heating composite materials comprising at least one first source of radiant energy, means to regulate the wave length of radiant energy given off by said at least one first source of radiant energy, at least one second source of radiant energy, means to regulate the wave length of radiant energy given off by said second source of radiant energy and means to move material to be heated past said first and said second heat sources wherein said radiant energy is predominantly infrared energy, said at least one first source is regulated to emit a predominant wave length of 3.5 microns and said at least one second source is regulated to emit a predominant wave length of about 5.5 microns and said at least one second source is downstream from said at least one first source.

2. The apparatus of claim 1 (10) further comprising means to apply cooling fluid to said radiant heat sources to regulate radiant heat from said sources.

3. The apparatus of claim 2 (10) further comprising means to contact said material to be heated with said cooling fluid after said cooling fluid passes over said radiant heaters.

4. The apparatus of claim 3 wherein heating of said article is at least partially by means of air also used as said means to regulate the wave length emitted by said first and second heaters.

5. Apparatus for activating a heat-shrinkable elastic on an article, such as a garment comprising conveyor means for feeding a plurality of said articles, said conveyor means including means for holding said articles in spaced relation with said elastic presented outwardly of said conveyor means, at least one first source of electromagnetic radiation, means to regulate the wave length of radiant energy emitted by said first source of radiant energy, means to bring said first source of radiant energy to an effective distance to apply radiant energy to said articles, at least one second source of radiant energy, means to regulate the wave length of radiant energy emitted by said at least one second source of radiant energy and means to bring said at least one second source of radiation within an effective distance to apply radiant energy to said shrinkable elastic wherein said radiant energy is predominantly infrared energy, said at least one first source is regulated to emit a predominant wave length of 3.5 microns and said at least one second source is regulated to emit a predominant wave length of about 5.5 microns and said at least one second source is downstream from said at least one first source.

6. The apparatus of claim 5 wherein said means to regulate said first and second sources of radiation comprises directing air past said sources of radiation.

7. The apparatus claimed in claim 5 wherein said elastic has an activation temperature above which it is caused to shrink, said conveyor means being substantially continuous in operation, said first and second radiation means extend along a length of said conveyor means, whereby said ribbons are irradiated by said irradiation means for a predetermined time period causing said ribbons to be heated to their activation temperature, and wherein the portion of said garment on which said elastic rests is heated predominantly by said at least one first source of radiation and said elastic predominantly by said second at least one second source of radiation.

* * * * *